(12) United States Patent
Kramer et al.

(10) Patent No.: US 11,261,141 B2
(45) Date of Patent: Mar. 1, 2022

(54) PROCESSES FOR ISOMERIZING ALPHA OLEFINS

(71) Applicant: ExxonMobil Chemical Patents Inc., Baytown, TX (US)

(72) Inventors: Anatoly I Kramer, Baytown, TX (US); Renyuan Yu, Humble, TX (US); Brett Thomas Loveless, Houston, TX (US); Wenyih F. Lai, Bridgewater, NJ (US); Mechilium J. G. Janssen, Kessel-Lo Leuven (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/767,894

(22) PCT Filed: Dec. 4, 2018

(86) PCT No.: PCT/US2018/063763
§ 371 (c)(1),
(2) Date: May 28, 2020

(87) PCT Pub. No.: WO2019/118230
PCT Pub. Date: Jun. 20, 2019

(65) Prior Publication Data
US 2020/0290940 A1    Sep. 17, 2020

Related U.S. Application Data

(60) Provisional application No. 62/598,656, filed on Dec. 14, 2017.

(51) Int. Cl.
*C07C 5/00* (2006.01)
*C07C 5/25* (2006.01)
*B01J 29/06* (2006.01)

(52) U.S. Cl.
CPC ............ *C07C 5/2518* (2013.01); *B01J 29/06* (2013.01); *C07C 2529/40* (2013.01); *C07C 2529/65* (2013.01)

(58) Field of Classification Search
CPC ................ C07C 5/00; C07C 5/22; C07C 5/23
See application file for complete search history.

(56) References Cited

U.S. PATENT DOCUMENTS

| | | |
|---|---|---|
| 2,952,719 A | 9/1960 | Appell et al. |
| 3,204,009 A | 11/1965 | Keith et al. |
| 3,405,196 A | 10/1968 | Wolff |
| 3,928,485 A | 12/1975 | Nagase et al. |
| 4,016,245 A | 4/1977 | Plank et al. |
| 4,076,842 A | 2/1978 | Plank et al. |
| 4,229,610 A | 10/1980 | Myers et al. |
| 4,556,477 A | 12/1985 | Dwyer |
| 4,684,760 A | 8/1987 | Drake |
| 4,711,873 A | 12/1987 | Suzukamo et al. |
| 4,749,819 A | 6/1988 | Hamilton, Jr. |
| 4,822,764 A | 4/1989 | Suzukamo et al. |
| 4,877,918 A | 10/1989 | Suzukamo et al. |
| 5,107,047 A | 4/1992 | Del Rossi et al. |
| 5,177,281 A * | 1/1993 | Haag .................. C07C 5/2518 585/324 |
| 5,194,244 A | 3/1993 | Brownscombe |
| 5,237,120 A | 9/1993 | Haag et al. |
| 5,246,566 A | 9/1993 | Miller |
| 5,252,527 A | 10/1993 | Zones |
| 5,589,442 A | 12/1996 | Gee et al. |
| 5,741,759 A | 4/1998 | Gee et al. |
| 5,965,783 A | 10/1999 | Gee et al. |
| 6,054,629 A | 4/2000 | Baralt et al. |
| 7,956,229 B2 | 6/2011 | Saruwatari et al. |

(Continued)

FOREIGN PATENT DOCUMENTS

| | | |
|---|---|---|
| CN | 102649674 | 8/2012 |
| JP | 63196526 | 8/1988 |

(Continued)

OTHER PUBLICATIONS

"Distribution of Silicone-to Aluminum Ratios in Zeolite ZSM-5", J. Chem. Soc., FaradayTrans., 1, Jan. 1, 1986, pp. 2645-2649.

(Continued)

*Primary Examiner* — Sharon Pregler
(74) *Attorney, Agent, or Firm* — ExxonMobil Chemical Patents Inc.—Law Department

(57) ABSTRACT

Processes are described for isomerizing one or more $C_4$-$C_{24}$ alpha olefins to produce an isomerization mixture comprising one or more $C_4$-$C_{24}$ internal olefins comprising contacting an olefinic feed comprising the one or more $C_4$-$C_{24}$ alpha olefins with a catalyst under isomerization conditions, wherein the catalyst comprises a microporous crystalline aluminosilicate selected from the group consisting of ZSM-5, ZSM-23, ZSM-35, ZSM-11, ZSM-12, ZSM-48, ZSM-57, and mixtures or combinations thereof, and wherein the microporous crystalline aluminosilicate has a $SiO_2/Al_2O_3$ molar ratio of less than or equal to about 100. The resulting isomerization mixture typically exhibits a lower pour point and maintained biodegradability properties as compared to the olefinic feed, and is particularly useful in drilling fluid and paper sizing compositions.

25 Claims, No Drawings

(56) References Cited

U.S. PATENT DOCUMENTS

| | | | |
|---|---|---|---|
| 2005/0070747 A1* | 3/2005 | Brown | C07C 5/2518 585/17 |
| 2006/0293549 A1 | 12/2006 | Sigl et al. | |
| 2009/0163757 A1* | 6/2009 | Gee | C07C 5/2518 585/671 |
| 2015/0322365 A1 | 11/2015 | Jeon et al. | |
| 2020/0369580 A1* | 11/2020 | Hill, Jr. | C07C 5/2518 |

FOREIGN PATENT DOCUMENTS

| | | |
|---|---|---|
| JP | 63196527 | 8/1988 |
| JP | 8040944 | 2/1996 |
| NL | 7209849 | 10/1972 |
| WO | 1996/011174 | 4/1996 |
| WO | 2005/031066 | 4/2005 |
| WO | 2008/124375 | 10/2008 |

OTHER PUBLICATIONS

Hattori H., et al., "Solid base catalysts: generation of basic sites and application to organic synthesis", Applied Catalysis, A: General 222, pp. 247-259, 2001.

Beres A., et al., "Layered double hydroxides and their pillared derivatives—materials for solid base catalysis; synthesis and characterization", Applied Catalysis, A: General 182, pp. 237-247, 1999.

* cited by examiner

PROCESSES FOR ISOMERIZING ALPHA OLEFINS

CROSS REFERENCE TO RELATED APPLICATIONS

This application is a national stage filing of International Patent Cooperation Treaty Application No. PCT/US2018/063763, filed Dec. 4, 2018, which claims priority from U.S. Provisional Application No. 62/598,656, filed Dec. 14, 2017, the disclosure of which is fully incorporated herein by reference.

This application claims the benefit of priority from U.S. Provisional Application No. 62/598,656, filed Dec. 14, 2017, which is incorporated herein by reference.

FIELD

The present disclosure relates to processes for isomerizing alpha olefins to produce an isomerization mixture comprising internal olefins.

BACKGROUND

Internal olefins are commercially valuable for use in a variety of applications, such as paper sizing agents and drilling fluids. For example, internal olefin based drilling fluids exhibit a number of enhanced properties, such as lower pour point, compared to alpha olefin based drilling fluids. For instance, U.S. Pat. No. 5,589,442 discloses synthetic hydrocarbon-based drilling fluids comprising mostly linear $C_{14}$ to $C_{18}$ olefins.

Internal olefins may be produced via the isomerization of alpha olefins. In the isomerization of alpha olefins to internal olefins for use in drilling fluids, it is desirable to produce an isomerization mixture having a combination of a reduced pour point while maintaining acceptable biodegradability. The pour point of the isomerization mixture generally decreases with increasing conversion of alpha olefins to internal olefins and with increasing formation of branched olefins. In contrast, the biodegradability of the isomerization mixture generally increases with decreased formation of branched olefins, particularly those having extended branching.

Accordingly, there is a need for highly active and selective methods of isomerizing alpha olefins to internal olefins at high conversion and with a controlled amount of branched olefin formation. References of potential interest may include: U.S. Pat. Nos. 5,741,759; 5,965,783; 6,054,629; 7,956,229; 5,107,047; 5,246,566; 4,749,819; 5,177,281; and U.S. Pat. No. U.S. 2005/0070747.

SUMMARY

According to the present disclosure, it has now been found that employing highly acidic, and therefore highly active, medium pore molecular sieve catalysts in the isomerization of $C_4$-$C_{24}$ alpha olefins advantageously allows for the isomerization to be conducted under mild process conditions, particularly at low temperature.

Thus, in one aspect, the present disclosure relates to a process for isomerizing one or more $C_4$-$C_{24}$ alpha olefins to produce an isomerization mixture comprising one or more $C_4$-$C_{24}$ internal olefins, the process comprising contacting an olefinic feed comprising the one or more $C_4$-$C_{24}$ alpha olefins with a catalyst under isomerization conditions, wherein the catalyst comprises a microporous crystalline aluminosilicate selected from the group consisting of ZSM-5, ZSM-23, ZSM-35, ZSM-11, ZSM-12, ZSM-48, ZSM-57, and mixtures or combinations thereof, and wherein microporous crystalline aluminosilicate has a $SiO_2/Al_2O_3$ molar ratio of less than or equal to about 100.

In a further aspect, the present disclosure relates to a drilling fluid comprising the isomerization mixture produced by the foregoing process.

In a yet further aspect, the present disclosure relates to a paper sizing composition comprising the isomerization mixture produced by the foregoing process.

DETAILED DESCRIPTION OF THE PREFERRED EMBODIMENTS

All numerical values within the detailed description and the claims herein are modified by "about" or "approximately" the indicated value, and take into account experimental error and variations that would be expected by a person having ordinary skill in the art. Unless otherwise indicated, room temperature is about 23° C.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first mixture are expressed based on the total weight of the first mixture. All ranges expressed herein should include both end points as two specific embodiments unless specified or indicated to the contrary.

Definitions

For the purpose of this specification and appended claims, the following terms are defined.

The term "hydrocarbon" means a class of compounds containing hydrogen bound to carbon, and encompasses (i) saturated hydrocarbon compounds; (ii) unsaturated hydrocarbon compounds; and (iii) mixtures of hydrocarbon compounds (saturated and/or unsaturated), including mixtures of hydrocarbon compounds having different values of n, i.e. differing carbon numbers.

As used herein, a "carbon number" refers to the number of carbon atoms in a hydrocarbon. Likewise, a "$C_x$" hydrocarbon is one having x carbon atoms (i.e., carbon number of x), and a "$C_x$-$C_y$" or "$C_{x-y}$" hydrocarbon is one having from x to y carbon atoms.

The term "alkane" refers to non-aromatic saturated hydrocarbons with the general formula $C_nH_{(2n+2)}$, where n is 1 or greater. An alkane may be straight chained or branched. Examples of alkanes include, but are not limited to methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

The term "olefin," alternatively referred to as "alkene," refers to a branched or unbranched unsaturated hydrocarbon having one or more carbon-carbon double bonds. A simple olefin comprises the general formula $C_nH_{2n}$, where n is 2 or greater. Examples of olefins include, but are not limited to ethylene, propylene, butylene, pentene, hexene and heptene. "Olefin" is intended to embrace all structural isomeric forms of an olefin. For example, butylene encompasses but-1-ene, (Z)-but-2-ene, etc.

As used herein, the term "molecular sieve" is used synonymously with the term "zeolite" or "microporous crystalline material."

As used herein, the term "reactor" refers to any vessel(s) in which a chemical reaction occurs. Reactor includes both distinct reactors, as well as reaction zones within a single reactor apparatus and, as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

As used herein, kinematic viscosity (KV) is measured using ASTM standard D-445 and reported at temperatures of 100° C. (KV100).

As used herein, pour point is measured according to ASTM D5950.

Various embodiments described herein provide processes for the production of one or more $C_4$-$C_{24}$ internal olefins via isomerization, typically catalytic isomerization, of one or more $C_4$-$C_{24}$ alpha olefins. It has been found that employing highly acidic, and therefore highly active, medium pore molecular sieve catalysts in the isomerization advantageously allows for the isomerization to be conducted under mild process conditions, particularly at low temperature. Conducting the isomerization at a low temperature provides several benefits, such as reducing energy usage of the process and improving selectivity to desired products in the resulting isomerization mixture.

Supply of Alpha Olefins

Generally, the alpha olefins supplied to the isomerization have a carbon number ranging from 4 to 24, more preferably from 14 to 20, more preferably from 15 to 18, and ideally from 16 to 18. Preferably, the alpha olefins supplied to the isomerization are linear alpha olefins.

Typically, the one or more $C_4$-$C_{24}$ alpha olefins are provided in an olefinic feed. Suitable olefinic feeds for use in various embodiments of the present invention comprise (or consist essentially of, or consist of) $C_4$-$C_{24}$ alpha olefins, preferably $C_{14}$-$C_{20}$ alpha olefins, such as $C_{15}$-$C_{18}$ alpha olefins, ideally $C_{16}$-$C_{18}$ alpha olefins. In any embodiment, at least about 50 wt %, preferably at least about 60 wt %, more preferably at least about 80 wt %, more preferably at least about 85 wt %, more preferably at least about 95 wt %, more preferably at least about 99 wt % of the olefinic feed is composed of alpha olefins, preferably alpha olefins, having any of the aforementioned $C_x$-$C_y$ ranges (i.e., any of the aforementioned numbers of carbon atoms) based on the total weight of the olefinic feed. For example, in any embodiment the olefinic feed may comprise from about 50 wt % to about 100 wt %, such as from about 75 wt % to about 90 wt %, of alpha olefins, preferably linear alpha olefins, having any of the aforementioned $C_x$-$C_y$ ranges based on the total weight of the olefinic feed. Particularly preferable olefinic feeds may comprise $C_{16}$-$C_{18}$ alpha olefins, ideally $C_{16}$/$C_{18}$ linear alpha olefin mixtures. In such aspects, the olefinic feed typically comprises at least about 40 wt % of $C_{16}$ alpha olefins, more preferably at least about 60 wt %, such as at least about 65 wt % of $C_{16}$ alpha olefins (preferably linear $C_{16}$ alpha olefins) based on the total weight of the olefinic feed and, additionally or alternatively, at most about 60 wt %, more preferably at most about 40 wt %, such as at most about 35 wt % of $C_{18}$ alpha olefins (preferably linear $C_{18}$ alpha olefins) based on the total weight of the olefinic feed, such as from about 60 wt % or from about 65 wt % to 75 wt % $C_{16}$ alpha olefins and from about 25% to about 40 wt % or to about 35 wt % $C_{18}$ alpha olefins based on the total weight of the olefinic feed.

In any embodiment, the olefinic feed preferably has an average carbon number (by weight, as measured by GC-MS) of greater than or equal to 14, preferably greater than or equal to 16, such as from 14 to 24.

Typically, the olefinic feed is substantially linear. For example, the olefinic feed typically has a branched olefin content of less than 10 wt % based on the total weight of the olefinic feed, preferably less than about 8 wt %, more preferably less about 4 wt %, such as from 0 wt % to 10 wt % branched olefin content based on the total weight of the olefinic feed.

Preferably, the olefinic feed is pretreated prior to isomerization to remove moisture, oxygenates, nitrates, and other impurities that could potentially deactivate the isomerization catalyst. Typically, the pretreatment is performed by passing the feed can be through a guard bed that contains a molecular sieve. Typically, the pretreated feed comprises less than about 50 ppmw water based on the weight of the feed, more preferably less than about 25 ppmw water.

Isomerization Catalyst

Generally, the isomerization is conducted in the presence of a catalyst. Typically, the isomerization catalyst comprises (or consists essentially of, or consists of) a microporous crystalline material (i.e., a molecular sieve), preferably a microporous crystalline aluminosilicate. Typically, suitable microporous crystalline aluminosilicates are those having a ten or twelve membered ring pore opening, channel or pocket. Preferred microporous crystalline aluminosilicates are those having a medium pore size and having a Constraint Index of 2-12 (as defined in U.S. Pat. No. 4,016,218, which is incorporated herein by reference), including e.g., ZSM-5, ZSM-23, ZSM-35, ZSM-11, ZSM-12, ZSM-48, ZSM-57 and mixtures or combinations thereof. For example, the microporous crystalline aluminosilicate may advantageously be selected from the group consisting of ZSM-11, ZSM-12, ZSM-48, ZSM-57, and mixtures or combinations thereof, such as ZSM-48 and/or ZSM-57. ZSM-5 is described in detail in U.S. Pat. No. 3,702,886 and Re. 29,948. ZSM-23 is described in U.S. Pat. No. 4,076,842. ZSM-35 is described in U.S. Pat. No. 4,016,245. The composition and method of manufacture of ZSM-11 are described in, for example, U.S. Pat. No. 3,709,979. The composition and method of manufacture of ZSM-12 are described in, for example, U.S. Pat. No. 4,556,477 and WO 93/25475. The composition and method of manufacture of ZSM-48 are described in, for example, U.S. Pat. No. 4,375,573. The composition and method of manufacture of ZSM-57 are described in, for example, EP-A-74,121 and U.S. Pat. No. 4,973,870. The entire contents of all the above patent specifications are incorporated herein by reference. In an especially preferred embodiment, the isomerization catalyst comprises (or consists essentially of, or consists of) a microporous crystalline aluminosilicate (or a molecular sieve) selected from the group consisting of ZSM-11, ZSM-12, ZSM-48, ZSM-57 and mixtures or combinations thereof, especially ZSM-48.

Preferred microporous crystalline aluminosilicates sieves are highly acidic. For example, preferably the microporous crystalline aluminosilicate has a $SiO_2/Al_2O_3$ molar ratio of less than about 100, such as less than about 75, or less than about 50, or less than about 40, or less than about 25, or less than about 10, or less than about 5, such as from about 5 to 100, or from about 20 to about 90, or from about 45 to about 70, or from about 70 to about 90, or from about 40 to about 50.

The isomerization catalyst may be composited with a porous matrix binder material such as clay and/or inorganic oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable inorganic oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form to facilitate extrusion of the catalyst composition. Typically, the binder material may be present from about 0 wt % to about 90 wt % based on the weight of the isomerization catalyst, such as from about 20 wt % to about 50 wt %.

Typically, the isomerization catalyst is free or substantially free of additional components apart from the microporous crystalline material, binder (if present), and optionally, trace amounts of alkali and/or alkali earth metals or compounds thereof. For example, in any embodiment the isomerization catalyst may be free or substantially free from promoters, such as noble metals and transition metals in metal or metal oxide form, e.g., platinum, palladium, ruthenium, iron, cobalt, and nickel. For instance, preferably the isomerization catalyst may comprise a combined platinum, palladium, ruthenium, iron, cobalt, and nickel content of less than about 0.5 wt % based on the weight of the isomerization catalyst, more preferably less than about 0.1 wt % or less than about 0.01 wt %.

Isomerization of Alpha Olefins

The isomerization reaction can be conducted in a wide range of reactor configurations including fixed bed (single or in series) and fluidized bed, preferably fixed bed. In addition, the isomerization can be conducted in a single reaction zone or in a plurality of reaction zones.

Typically, the isomerization is conducted under conditions suitable to maintain the reaction medium in the liquid phase. Preferably, the isomerization is conducted under mild process conditions, particularly at low temperature. Suitable reaction temperatures range from about 50° C. to about 200° C., such as from about 100° C. to about 180° C., or from about 110° C. to about 170° C., or from about 130° C. to about 150° C., while suitable isomerization pressures range from about 2 kPa absolute to about 7,000 kPa absolute, such as from about 5 psig (136 kPa-a) to about 200 psig (1480 kPa-a). Preferably, the olefinic feed is supplied to the reaction at a weight hourly space velocity (WHSV) ranging from about 1 $h^{-1}$ to about 50 $h^{-1}$, more preferably from about 2 $h^{-1}$ to about 20 $h^{-1}$.

Typically, the isomerization exhibits a high single-pass rate of conversion (measured as 100 minus the remaining amount of LAO expressed in wt %, as measured by GC-MS). For example, preferably the single-pass rate of conversion of the one or more $C_4$-$C_{24}$ alpha olefins is at least about 40%, more preferably at least about 50%, and ideally at least about 75%. In such aspects, the isomerization can be conveniently conducted in the absence of recycle, i.e., without recycling any portion of the produced isomerization mixture. Preferably, conducting the isomerization without recycle provides several process advantages, such as increasing process reliability and reducing operating costs.

Preferably, the isomerization reaction is highly selective to the desired internal olefin products, particularly linear internal olefins, and exhibits minimal side reactions, such as skeletal isomerization, oligomerization, and cracking. For example, typically less than about 10 wt % of $C_4$-$C_{24}$ alpha olefins present in the olefinic feed are converted to product having a lower or higher carbon number. Additionally or alternatively, typically from about 5 wt % to about 30 wt % of linear $C_4$-$C_{24}$ alpha olefins present (if any) in the olefinic feed are converted to branched olefins.

Isomerization Mixture

The resulting isomerization mixture obtained via isomerization of the one or more $C_4$-$C_{24}$ alpha olefins according to any one or more of the foregoing embodiments typically comprises (or consists essentially of, or consists of) linear internal olefins, and optionally, branched olefins, e.g., branched internal olefins. For example, the isomerization mixture typically comprises at least about 40 wt %, preferably at least about 60 wt %, more preferably at least about 80 wt %, such as at least about 85 wt %, or at least about 95 wt %, or even at least about 99 wt % of linear internal olefins based on the total weight of the isomerization mixture. The isomerization mixture preferably has a branched olefin content of less than about 35 wt %, preferably less than about 20 wt %, such as less than about 10 wt %, or less than about 8 wt % based on the total weight of the isomerization mixture, such as from about 5 wt % to about 30 wt %, or from about 8 wt % to about 15 wt %, or from about 0 wt % to about 10 wt %.

The isomerization product may also contain some amount of residual $C_4$-$C_{24}$ alpha olefins. Preferably, the isomerization mixture comprises a residual alpha olefin content of less than about 35 wt %, preferably less than about 10 wt %, and ideally less than about 5 wt % based on the total weight of the isomerization mixture.

The obtained isomerization mixture may be particularly useful in drilling fluid compositions and paper sizing compositions. Preferred isomerization mixtures suitable for drilling fluid compositions generally comprise 50 wt % or more of $C_{16}$-$C_{18}$ linear internal olefins. Such mixtures may be particularly useful as the oil-phase in drilling fluid compositions comprising oil-based drilling emulsions.

When used for drilling fluid compositions, the isomerization mixture may generally exhibit any one or more of the following properties:

KV100 within the range from about 1 cSt to about 2 cSt, preferably from about 1 to about 1.1 cSt to about 1.5 cSt;

Pour point of −6° C. or less, such as −10° C. or less, such as −12° C. or less, such as −15° C. or less.

Additionally or alternatively, when used for drilling fluid compositions the isomerization mixture is typically biodegradable under aerobic and preferably anaerobic conditions. Particularly preferably, the isomerization mixture and drilling fluid compositions comprising the same meet or exceed the anaerobic biodegradability standard set forth in the Marine Closed Bottle Biodegradation Test System: EPA METHOD 1647.

The following examples illustrate the present invention. Numerous modifications and variations are possible and it is to be understood that within the scope of the appended claims, the invention may be practiced otherwise than as specifically described herein.

EXAMPLES

Gas Chromatography Procedure

Liquid samples from the reactor effluent were analyzed on an Agilent 7890 Gas Chromatograph (GC) equipped with FID detectors and automatic liquid samplers (ALS). Two GC methods were employed to analyze the samples—one for measuring the linear alpha olefin (LAO) content and the other for measuring the branched olefin (BO) content. The typical injection size for both methods was about 0.2 µl.

For the LAO content measurement method, the column used was Agilent DB-WAX (60 m×250 µm×0.25 µm). The GC was operated in constant flow mode at 40 psi (280 kPa) inlet pressure and with column flow of 1.839 mL/min using helium as a carrier gas. The following oven procedure was used:

Initial temperature of 140° C., hold for 17 minutes;
Ramp at 25° C./min to 240° C., hold for 8 minutes;
Total analysis time of 29 minutes.

For the BO content measurement method, liquid sample was first fully hydrogenated to saturated material, from which the BO content was determined by analyzing the total branched aliphatic material. The column used was Agilent HP-1 (60 m×250 µm×1 µm) and the inlet liner was a split inlet liner (obtained from Agilent) that was pre-packed with 1 cm height 1% Pt/Al$_2$O$_3$. The GC was operated in ramped pressure mode with an initial pressure of 20 psi (140 kPa) to 50 psi (340 kPa) at 7 psi/min (50 kPa/min) using hydrogen as a carrier gas.

The following oven procedure was used:
Initial temperature of 140° C., hold for 17 minutes;
Ramp at 25° C./min to 240° C., hold for 8 minutes;
Total analysis time of 29 minutes.

The LIO content can be assessed as LIO=100−LAO content−BO content.

$^1$H NMR Procedure

NMR spectra were acquired using a 500 MHz spectrometer obtained from Bruker Corporation, with chloroform-d used as the solvent.

Measurement of Alpha Value

The Alpha Value tests for the materials or compositions in the Examples were performed in accordance with the methods described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test included a constant temperature of 538° C. and a variable flow rate as described in detail in the Journal of Catalysis, Vol. 61, p. 395 (1980).

Measurement of Total Surface Area by BET

The total BET was measured by nitrogen adsorption/desorption with a Micromeritics Tristar II 3020 instrument after degassing of the calcined catalyst material for 4 hrs at 350° C. More information regarding the method can be found, for example, in "Characterization of Porous Solids and Powders: Surface Area, Pore Size and Density", S. Lowell et al., Springer, 2004.

Example 1

ZSM-48 Catalyst Composition Synthesis

High activity, small ZSM-48 crystals having a silica to alumina (SiO$_2$/Al$_2$O$_3$) molar ratio of either ~70 or 90 were synthesized according to the "as-synthesized" ZSM-48 crystal preparation methods described in U.S. Pat. No. 7,482,300 at col. 3 line 53 to col. 6 line 15. The XRD pattern of the as-synthesized material showed the typical pure phase of ZSM-48 topology. The SEM of the as-synthesized material showed that the material was composed of agglomerates of small crystals.

The as-synthesized crystals were calcined for 3 hours in nitrogen at ~1000° F. (~538° C.), ammonium exchanged with ~1N ammonium nitrate solution to remove sodium, and calcined for 6 hours in air at ~1000° F. (~538° C.).

The resulting H-formed crystals having a SiO$_2$/Al$_2$O$_3$ of 90 exhibited an Alpha Value of ~100, hexane sorption of 49 mg/g, and surface area of 299 m$^2$/g. The resulting H-formed crystals having a SiO$_2$/Al$_2$O$_3$ of 70 exhibited an Alpha Value of ~120, hexane sorption of ~53 mg/g, and surface area of 328 m$^2$/g.

Examples 2-5

Isomerization of C16 LAO Feed with ZSM-48 in a Batch Reactor

The isomerization tests described in Examples 2-5 were carried out in a Parr reactor equipped with a stirrer and temperature control. The ZSM-48 catalyst prepared in Example 1 having a silica to alumina molar ratio of either 70 or 90 was sized to 30 to 75 microns in powder form, loaded into the reactor (either 1 or 2 grams), and activated/pretreated overnight (~8-10 hours) with a purge of N$_2$ at 250° C. About 150 grams of a C$_{16}$ LAO feed (Alphaplus™ 1-Hexadecene, commercially available from ChevronPhillips Chemical Company LLC) was preheated to the reaction temperature (150° C. or 180° C.) before being introduced into the Parr reactor. The isomerization reaction was conducted as a slurry of catalyst with the LAO feed with stirring of the reactor contents at 500 rpm over the duration of the reaction. Normal testing conditions were at 150° C. or 180° C., ambient pressure (~1 bar), and a reaction time ranging from 50 minutes to 8 hours.

The resulting reaction product was removed from the reactor, cooled to room temperature, and filtered. The filtered product was characterized by proton nuclear magnetic resonance ($^1$H NMR) to determine the relative amount of unreacted LAO in the produced isomerization mixture and the relative amounts of linear internal olefins (LIO) and branched olefins (BO) in the produced isomerization mixture. Table 1 summarizes the catalyst loading, catalyst acidity (Si to Al$_2$ ratio), and reaction conditions for Examples 2-5, while Table 2 summarizes the composition of the resulting isomerization mixtures.

TABLE 1

|  | Ex. 2 | Ex. 3 | Ex. 4 | Ex. 5 |
| --- | --- | --- | --- | --- |
| Catalyst Loading (g) | 1 | 1 | 2 | 2 |
| Catalyst SiO$_2$/Al$_2$O$_3$ Molar Ratio | 90 | 90 | 90 | 70 |
| C16 LAO Feed Loading (g) | 150 | 150 | 150 | 150 |
| T (° C.) | 150 | 150 | 180 | 150 |
| Reaction Duration (h) | 4 | 8 | 4 | 0.8 |

TABLE 2

|  | Ex. 2 | Ex. 3 | Ex. 4 | Ex. 5 |
|---|---|---|---|---|
| LIO (wt %) | ~70-85 | ~70-80 | ~45-55 | ~80-85 |
| BO (wt %) | ~5-7 | ~6-9 | ~30-40 | ~5-7 |
| LAO (wt %) | <5 | <5 | <5 | <5 |

Examples 2-5 demonstrate that the isomerization reaction using high acidity ZSM-48 as the isomerization catalyst exhibited high LAO conversion and selectivity towards the desired LIO (e.g., resulting in at least about 45 wt % LIO in the isomerization mixture) under mild reaction conditions, particularly at 150° C.

Example 6

ZSM-57 Catalyst Composition Synthesis

High activity ZSM-57 crystals having a $SiO_2/Al_2O_3$ molar ratio of ~40 were synthesized according to the methods described in U.S. Pat. No. 4,873,067 at col. 6 line 25 to col. 7 line 47. The XRD pattern of the as-synthesized material showed the typical pure phase of ZSM-57 topology. The SEM of the as-synthesized material showed that the material was composed of thin layered morphology crystals.

The as-synthesized crystals were calcined for 3 hours in nitrogen at ~1000° F. (~538° C.), ammonium exchanged with ~1N ammonium nitrate solution to remove sodium, and calcined for 6 hours in air at ~1000° F. (~538° C.).

The resulting H-formed crystals having a $SiO_2/Al_2O_3$ molar ratio of 40 exhibited an Alpha Value of ~700, hexane sorption of ~74 mg/g, and surface area of 500 m²/g.

Examples 7-8

Isomerization of C16 LAO Feed with ZSM-57 in a Batch Reactor

The isomerization tests described in Examples 7-8 were carried out in a 30 mL scintillation vial equipped with a magnetic stirrer. The ZSM-57 catalyst prepared in Example 6 (1 gram) in powder form, sized to 30 to 75 microns, was loaded into the scintillation vial and activated/pretreated for 2 hours with a purge of $N_2$ at 130° C. (Ex. 7) or 110° C. (Ex. 8). About 10 grams of a $C_{16}$ LAO feed (Alphaplus™ 1-Hexadecene, commercially available from ChevronPhillips Chemical Company LLC) was injected into the heated vial via syringe. The isomerization reaction was conducted as a slurry of catalyst with the LAO feed with stirring of the reactor contents at 500 rpm over the duration of the reaction. Normal testing conditions were at 130° C. or 110° C., ambient pressure (~1 bar), and a reaction time of 4 hours.

The resulting reaction product was removed from the reactor, cooled to room temperature, and filtered. The filtered product was characterized by proton nuclear magnetic resonance (¹H NMR) to determine the relative amount of unreacted LAO in the produced isomerization mixture and the relative amounts of LIO and BO in the produced isomerization mixture. Table 3 summarizes the catalyst loading, catalyst acidity (silica to alumina ratio), reaction conditions and results for Examples 7-8, and Table 4 summarizes the composition of the resulting isomerization mixtures.

TABLE 3

Reaction Conditions of Examples 7-8

|  | Ex. 7 | Ex. 8 |
|---|---|---|
| Catalyst Loading (g) | 1 | 1 |
| Catalyst $SiO_2/Al_2O_3$ Molar Ratio | 45 | 45 |
| C16 LAO Feed Loading (g) | 10 | 10 |
| T (° C.) | 130 | 110 |
| Reaction Duration (h) | 4 | 4 |

TABLE 4

Isomerization Mixture Compositions of Examples 7-8

|  | Ex. 7 | Ex. 8 |
|---|---|---|
| LIO (wt %) | ~86 | ~65 |
| BO (wt %) | ~13 | ~12 |
| LAO (wt %) | ~1 | ~22 |

Examples 7-8 demonstrate high LAO conversion (e.g., greater than about 75%) and selectivity towards the desired LIO (e.g., resulting in at least about 65 wt % LIO in the isomerization mixture) using high acidity ZSM-57 as the isomerization catalyst under mild reaction conditions, particularly at 130° C.

Example 9

ZSM-12 Extrudate Catalyst Composition Synthesis

ZSM-12 crystals prepared in accordance with the methods of U.S. Pat. No. 6,893,624 at col. 4 line 27 to col. 5 line 35 and having a $SiO_2/Al_2O_3$ molar ratio of ~45 were used to prepare a 65 wt % zeolite/35 wt % alumina particle in accordance with the following procedure. 65 parts by weight, on a calcined at 538° C. basis, of the ZSM-12 crystals were mulled with 35 parts by weight, on a calcined at 538° C. basis, of Versal-300 pseudoboehmite alumina binder (commercially available from UOP LLC). Sufficient amount of water was added to make an extrudable paste, after which the resulting paste was extruded into 1/16" (0.16 cm) quadrulobe extrudates and then dried at 121° C. overnight. The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 590, hexane sorption of 37.5 mg/g, and surface area of ~277 m²/g.

Example 10

ZSM-11 Extrudate Catalyst Composition Synthesis

ZSM-11 crystals prepared in accordance with the methods of U.S. Pat. No. 3,709,979 at col. 4 line 14 to col. 6 line 37 and having a $SiO_2/Al_2O_3$ molar ratio of ~50 were used to prepare a 65 wt % zeolite/35 wt % alumina particle in accordance with the following procedure. First, 65 parts by weight, on a calcined at 538° C. basis, of the ZSM-11 crystals were mulled with 35 parts by weight, on a calcined at 538° C. basis, of Versal-300 pseudoboehmite alumina binder (commercially available from UOP LLC). Sufficient amount of water was added to make an extrudable paste, after which the resulting paste was extruded into 1/16" (0.16 cm) quadrulobe extrudates and then dried at 121° C. overnight. The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 350, hexane sorption of 76.2 mg/g, and surface area of ~415 m$^2$/g.

Example 11

ZSM-57 Extrudate Catalyst Composition Synthesis

ZSM-57 crystals prepared in accordance with the methods of U.S. Pat. No. 4,873,067 at col. 6 line 25 to col. 7 line 47 and having a SiO$_2$/Al$_2$O$_3$ molar ratio of ~40 were used to prepare a 65 wt % zeolite/35 wt % alumina particle in accordance with the following procedure. First, 65 parts by weight, on a calcined at 538° C. basis, of the ZSM-57 crystals were mulled with 35 parts by weight, on a calcined at 538° C. basis, of Versal-300 pseudoboehmite alumina binder (commercially available from UOP LLC). Sufficient amount of water was added to make an extrudable paste, after which the resulting paste was extruded into 1/16" (0.16 cm) quadrulobe extrudates and then dried at 121° C. overnight. The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 380, hexane sorption of 56.1 mg/g, and surface area of ~371 m$^2$/g.

Example 12

ZSM-48 Extrudate Catalyst Composition Synthesis

ZSM-48 crystals prepared in accordance with "as-synthesized" ZSM-48 crystal preparation methods described in U.S. Pat. No. 7,482,300 at col. 3 line 53 to col. 6 line 15 and having a SiO$_2$/Al$_2$O$_3$ molar ratio of ~70 were used to prepare a 65 wt % zeolite/35 wt % alumina particle in accordance with the following procedure. First, 65 parts by weight, on a calcined at 538° C. basis, of the ZSM-48 crystals were mulled with 35 parts by weight, on a calcined at 538° C. basis, of Versal-300 pseudoboehmite alumina binder (commercially available from UOP LLC). Sufficient amount of water was added to make an extrudable paste, after which the resulting paste was extruded into 1/16" (0.16 cm) quadrulobe extrudates and then dried at 121° C. overnight. The dried extrudate material was calcined in nitrogen at 538° C. for 3 hours. The nitrogen calcined extrudate was humidified with saturated air and exchanged with 1 N ammonium nitrate to reduce the sodium content to a level of <500 ppmw. After ammonium nitrate exchange, the extrudate was washed with deionized water to remove residual nitrate ions, subsequently dried at 121° C. overnight, and lastly calcined in air at 538° C. for 3 hours. The resulting H-formed extrudate exhibited an Alpha Value of 65, hexane sorption of 40.9 mg/g, and surface area of ~301 m$^2$/g.

Examples 13-16

Catalytic Activity of Various Zeolite Catalysts in Isomerization of C16/C18 (65:35) LAO Feed in a Fixed Bed Reactor A study of the four zeolite-based catalysts prepared in accordance with Examples 9-11 for the isomerization of a C$_{16}$/C$_{18}$ LAO feed was conducted in a continuous, isothermal, tubular fixed bed reactor. The catalysts employed during each example are shown in Table 5.

TABLE 5

Isomerization Catalysts of Examples 13-16

| Example | Catalyst | Zeolite SiO$_2$/Al$_2$O$_3$ Molar Ratio |
|---|---|---|
| 13 | ZSM-12 Extrudate (Ex. 9) | 45 |
| 14 | ZSM-11 Extrudate (Ex. 10) | 50 |
| 15 | ZSM-57 Extrudate (Ex. 11) | 45 |
| 16 | ZSM-48 Extrudate (Ex. 12) | 70 |

In each experiment, 1.54 g of the formulated catalyst and ~15-20 g of silicon carbide (SiC) was loaded into the reactor. The catalyst was loaded between two separate sections of SiC such that it was securely positioned in isothermal zone the isothermal zone of the reactor. A 65 wt % C$_{16}$/35 wt % C$_{18}$ LAO feed (a blend of Alphaplus™ 1-Hexadecene and Alphaplus™ 1-Octadecene, both available from ChevronPhillips Chemical Company LLC) containing ~7 wt % BO (as determined by GC) was pretreated by being passed through a guard bed containing a molecular sieve and then introduced into the reactor at a WHSV of 2.5 h$^{-1}$ for a total reaction time of 70 hours. The isomerization reaction was conducted at a temperature of 130° C. and a pressure of 20 psig (239 kPa-a).

The resulting isomerization product mixture were sampled online. The collected samples after 70 hours of reaction time were analyzed by GC for composition and were also measured for pour point. Table 6 summarizes the compositions and pour point properties of the isomerization mixtures.

TABLE 6

Isomerization Mixture Compositions and Pour Points of Examples 13-16

|  | Ex. 13 | Ex. 14 | Ex. 15 | Ex. 16 |
|---|---|---|---|---|
| LIO (wt %) | 83.1 | 84.0 | 60.9 | 83.1 |
| BO (wt %) | 8.4 | 7.9 | 7.5 | 8.3 |
| LAO (wt %) | 8.5 | 8.1 | 31.6 | 8.6 |
| Pour Point (° C.) | −0.1 | −3.30 | 3.40 | −10.7 |

As seen from Table 6, high LAO conversion and selectivity towards the desired LIO was observed for the four tested isomerization catalysts, as well as minimal production of branched olefins.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including" for purposes of United States law. Likewise whenever a composition, an element or a group of elements is preceded with the transitional phrase "comprising", it is understood that it is also contemplated that the same composition or group of elements with transitional phrases "consisting essentially of," "consisting of", "selected from the group of consisting of," or "is" preceding the recitation of the composition, element, or elements and vice versa.

Additionally or alternately, embodiments disclosed herein relate to:

Embodiment 1: A process for isomerizing one or more $C_4$-$C_{24}$ alpha olefins to produce an isomerization mixture comprising one or more $C_4$-$C_{24}$ internal olefins, the process comprising contacting an olefinic feed comprising the one or more $C_4$-$C_{24}$ alpha olefins with a catalyst under isomerization conditions, wherein the catalyst comprises a microporous crystalline aluminosilicate selected from the group consisting of ZSM-5, ZSM-23, ZSM-35, ZSM-11, ZSM-12, ZSM-48, ZSM-57, and mixtures or combinations thereof, and wherein microporous crystalline aluminosilicate has a $SiO_2$/$Al_2O_3$ molar ratio of less than or equal to about 100.

Embodiment 2: The process of embodiment 1, wherein the microporous crystalline aluminosilicate has a $SiO_2$/$Al_2O_3$ molar ratio within the range from about 20 to about 90.

Embodiment 3: The process of embodiment 1 or 2, wherein the microporous crystalline aluminosilicate is selected from the group consisting of ZSM-11, ZSM-12, ZSM-48, ZSM-57, and mixtures or combinations thereof.

Embodiment 4: The process of any one of embodiments 1 to 3, wherein the microporous crystalline aluminosilicate is selected from the group consisting of ZSM-48, ZSM-57, and mixtures or combinations thereof.

Embodiment 5: The process of any one of embodiments 1 to 4, wherein the catalyst further comprises a binder selected from the group consisting of clay, inorganic oxides, and mixtures or combinations thereof.

Embodiment 6: The process of any one of embodiments 1 to 5, wherein the catalyst is free or substantially free of noble metals and/or transition metals.

Embodiment 7: The process of any one of embodiments 1 to 6, wherein the olefinic feed has an average carbon number of greater than or equal to 14.

Embodiment 8: The process of any one of embodiments 1 to 7, further comprising passing the olefinic feed through a guard bed prior to contacting with the catalyst.

Embodiment 9: The process of any one of embodiments 1 to 8, wherein the olefinic feed comprises $C_{16}$ alpha olefins at a concentration of at least about 40 wt % based on the total weight of the olefinic feed.

Embodiment 10: The process of embodiment 9, wherein the olefinic feed comprises $C_{16}$ alpha olefins at a concentration of at least about 60 wt %, preferably at least about 65 wt % based on the total weight of the olefinic feed, and wherein the olefinic feed comprises $C_{18}$ alpha olefins at a concentration of at most about 40 wt %, preferably at most about 35 wt % based on the total weight of the olefinic feed.

Embodiment 11: The process of any one of embodiments 1 to 10, wherein the isomerization conditions comprise a temperature from about 50° C. to about 200° C.

Embodiment 12: The process of embodiment 11, wherein the temperature ranges from about 100° C. to about 180° C.

Embodiment 13: The process of any one of embodiments 1 to 12, wherein the olefinic feed is supplied at a weight hourly space velocity (WHSV) from about 1 h$^{-1}$ to about 50 h$^{-1}$.

Embodiment 14: The process of embodiment 13, wherein the WHSV of the olefinic feed ranges from about 2 h$^{-1}$ to about 20 h$^{-1}$.

Embodiment 15: The process of any one of embodiments 1 to 14, wherein the rate of conversion of the $C_4$-$C_{24}$ alpha olefins to the $C_4$-$C_{24}$ internal olefins is at least about 40%.

Embodiment 16: The process embodiment 15, wherein the rate of conversion of the $C_4$-$C_{24}$ alpha olefins to the $C_4$-$C_{24}$ internal olefins is at least about 75%.

Embodiment 17: The process of any one of embodiments 1 to 16, wherein the isomerization mixture comprises linear internal olefins at a concentration of about 40 wt % or more based on the total weight of the isomerization mixture.

Embodiment 18: The process of embodiment 17, wherein the isomerization mixture comprises linear internal olefins at a concentration of about 60 wt % or more based on the total weight of the isomerization mixture.

Embodiment 19: The process of any one of embodiments 1 to 18, wherein the isomerization mixture comprises branched olefins at a concentration of about 35 wt % or less based on the total weight of the isomerization mixture.

Embodiment 20: The process of embodiment 19, wherein the isomerization mixture comprises branched olefins at a concentration ranging from about 5 wt % to about 35 wt % based on the total weight of the isomerization mixture.

Embodiment 21: The process of any one of embodiments 1 to 20, wherein the isomerization mixture comprises linear alpha olefins at a concentration of less than about 35 wt % based on the total weight of the isomerization mixture.

Embodiment 22: The process of embodiment 21, wherein the isomerization mixture comprises linear alpha olefins at a concentration of less than about 10 wt % based on the total weight of the isomerization mixture.

Embodiment 23: The process of any one of embodiments 1 to 22, wherein the isomerization mixture has a pour point of about −6° C. or less.

Embodiment 24: A drilling fluid comprising the isomerization mixture produced by any one of embodiments 1 to 23.

Embodiment 25: A paper sizing composition comprising the isomerization mixture produced by any one of embodiments 1 to 23.

The invention claimed is:

1. A process for isomerizing one or more $C_4$-$C_{24}$ alpha olefins to produce an isomerization mixture comprising one or more $C_4$-$C_{24}$ internal olefins, the process comprising contacting an olefinic feed comprising the one or more $C_4$-$C_{24}$ alpha olefins with a catalyst under isomerization conditions, wherein the catalyst comprises a microporous crystalline aluminosilicate selected from the group consisting of ZSM-5, ZSM-23, ZSM-35, ZSM-11, ZSM-12, ZSM-48, ZSM-57, and mixtures or combinations thereof, and wherein microporous crystalline aluminosilicate has a $SiO_2$/$Al_2O_3$ molar ratio of less than or equal to about 100 and greater than or equal to 40, and wherein the olefinic feed is supplied at a weight hourly space velocity (WHSV) from 2 h$^{-1}$ to 50 h$^{-1}$.

2. The process of claim 1, wherein the microporous crystalline aluminosilicate has a $SiO_2$/$Al_2O_3$ molar ratio within the range from about 20 to about 90.

3. The process of claim 1, wherein the microporous crystalline aluminosilicate is selected from the group consisting of ZSM-11, ZSM-12, ZSM-48, ZSM-57, and mixtures or combinations thereof.

4. The process of claim 3, wherein the microporous crystalline aluminosilicate is selected from the group consisting of ZSM-48, ZSM-57, and mixtures or combinations thereof.

5. The process of claim 1, wherein the catalyst further comprises a binder selected from the group consisting of clay, inorganic oxides, and mixtures or combinations thereof.

6. The process of claim 5, wherein the catalyst is free or substantially free of noble metals and/or transition metals.

7. The process of claim 1, wherein the olefinic feed has an average carbon number of greater than or equal to 14.

8. The process of claim 1, further comprising passing the olefinic feed through a guard bed prior to contacting with the catalyst.

9. The process of claim 1, wherein the olefinic feed comprises $C_{16}$ alpha olefins at a concentration of at least 40 wt % based on the total weight of the olefinic feed.

10. The process of claim 9, wherein the olefinic feed comprises $C_{16}$ alpha olefins at a concentration of at least 65 wt % based on the total weight of the olefinic feed, and wherein the olefinic feed comprises $C_{18}$ alpha olefins at a concentration of at most 35 wt % based on the total weight of the olefinic feed.

11. The process of claim 1, wherein the isomerization conditions comprise a temperature from 50° C. to 200° C.

12. The process of claim 11, wherein the temperature ranges from 100° C. to 180° C.

13. The process of claim 1, wherein the WHSV of the olefinic feed ranges from 2 h$^{-1}$ to 20 h$^{-1}$.

14. The process of claim 1, wherein the rate of conversion of the $C_4$-$C_{24}$ alpha olefins to the $C_4$-$C_{24}$ internal olefins is at least 40%.

15. The process of claim 14, wherein the rate of conversion of the $C_4$-$C_{24}$ alpha olefins to the $C_4$-$C_{24}$ internal olefins is at least about 75%.

16. The process of claim 1, wherein the isomerization mixture comprises linear internal olefins at a concentration of 40 wt % or more based on the total weight of the isomerization mixture.

17. The process of claim 16, wherein the isomerization mixture comprises linear internal olefins at a concentration of 60 wt % or more based on the total weight of the isomerization mixture.

18. The process of claim 1, wherein the isomerization mixture comprises branched olefins at a concentration of 35 wt % or less based on the total weight of the isomerization mixture.

19. The process of claim 18, wherein the isomerization mixture comprises branched olefins at a concentration ranging from 5 wt % to 35 wt % based on the total weight of the isomerization mixture.

20. The process of claim 1, wherein the isomerization mixture comprises linear alpha olefins at a concentration of less than 35 wt % based on the total weight of the isomerization mixture.

21. The process of claim 20, wherein the isomerization mixture comprises linear alpha olefins at a concentration of less than 10 wt % based on the total weight of the isomerization mixture.

22. The process of claim 1, wherein the isomerization mixture has a pour point of −6° C. or less.

23. A drilling fluid comprising the isomerization mixture produced by claim 1.

24. A paper sizing composition comprising the isomerization mixture produced by claim 1.

25. The process of claim 1, wherein the microporous crystalline aluminosilicate has a $SiO_2/Al_2O_3$ molar ratio within the range of 45 to 90.

* * * * *